United States Patent [19]

Peterson

[11] 4,175,053

[45] Nov. 20, 1979

[54] BASE REACTANT

[75] Inventor: Donald J. Peterson, Cincinnati, Ohio

[73] Assignee: The Procter & Gamble Company, Cincinnati, Ohio

[21] Appl. No.: 731,176

[22] Filed: Oct. 12, 1976

[51] Int. Cl.$^2$ .................. C09K 3/00; C11D 13/00; C07C 29/14; C07C 17/26

[52] U.S. Cl. ........................... 252/192; 252/41; 252/156; 252/367; 260/415; 260/417; 260/648 R; 568/853

[58] Field of Search ............... 252/192, 41, 108, 367, 252/369; 260/415, 417, 465.1

[56] References Cited

U.S. PATENT DOCUMENTS

| | | | |
|---|---|---|---|
| 2,753,364 | 7/1956 | Boner et al. | 260/413 |
| 3,133,942 | 5/1964 | Hahl | 260/414 |
| 3,201,451 | 8/1965 | Idol et al. | 260/465.1 |
| 3,936,490 | 2/1976 | Hofmann et al. | 260/465.3 |

FOREIGN PATENT DOCUMENTS 1543450  9/1969  Fed. Rep. of Germany ........ 260/465.1

OTHER PUBLICATIONS

Rappoport, The Chemistry of the Cyano Group, Pub. 1970, pp. 168, 169 and 256–258.

Primary Examiner—Herbert B. Guynn
Attorney, Agent, or Firm—Walter L. Stumpf; Jerry J. Yetter; Richard C. Witte

[57] ABSTRACT

Alkyl nitriles in combination with alkali metal hydroxides provide super bases which are useful in various chemical processes.

5 Claims, No Drawings

BASE REACTANT

BACKGROUND OF THE INVENTION

The present invention encompasses compositions of matter which exhibit highly basic properties and which can properly be classified in the group of materials known as "super bases". More specifically, alkali metal hydroxides in combination with liquid alkyl nitriles provide highly basic systems which are useful in a variety of chemical processes.

Recently, it has been discovered that the basicities of crown ether-alkali metal hydroxide complexes are substantially greater than the basicities of the corresponding hydroxides in simple hydroxylic solvents. Apparently, in the presence of a crown ether the hydroxyl ion is substantially non-solvated and is free to act as a more potent base than when in the more familiar water- or alcohol-solvated form. Such bases have become known as "super bases", a term which reflects their potent basic properties. The use of super bases in a variety of organic syntheses has demonstrated their superiority over aqueous bases for certain types of reactions. For example, the super bases are particularly useful for preparing carbanion and/or carbene intermediates which, in turn, will react with a number of other materials to provide a variety of useful organic compounds.

While the crown ethers are useful in the preparation of super bases, they are relatively expensive and are not particularly attractive for use on a commercial scale. Moreover, there is some question of the safety of the crown ethers, some of which may exhibit untoward effects on the central nervous system. These crown ether materials are discussed more fully in the article by C. J. Pedersen, *J. Amer. Chem. Soc.* 89 (26) 7017-36 (1967).

The present invention provides super bases without the need for crown ethers. In the practice of this invention, alkali metal hydroxides are combined with alkyl nitriles to provide super bases which are useful in a variety of organic syntheses.

The copending applications of Peterson, the inventor herein, entitled SOAP MAKING, Ser. No. 731,183, filed Oct. 12, 1976, now U.S. Pat. No. 4,129,520, HYDRATED SOAP MAKING, Ser. No. 731,163, filed Oct. 12, 1976, now U.S. Pat. No. 4,075,234, and ENERGY SAVING DETERGENT MANUFACTURE, Ser. No. 731,182, filed Oct. 12, 1976, now U.S. Pat. No. 4,129,516, the disclosures of which are incorporated herein by reference, describe means for preparing substantially anhydrous and/or low moisture content soaps without the need for a heat drying step using super base compositions of the type disclosed herein.

RELATED REFERENCES

The alkyl nitriles used herein are well-known materials. Acetonitrile (methyl cyanide; cyanomethane; ethanenitrile) is a highly preferred alkyl nitrile for use in the present invention. As noted in THE MERCK INDEX, Seventh Ed., Page 8, this material is reported to be a medium for producing reactions involving ionization, as a solvent in non-aqueous titrations, and as a non-aqueous solvent for inorganic salts.

The use of acetonitrile as an extraction solvent for separating/removing various materials from compositions containing fatty acids, sterols, and the like, is disclosed in the following references: U.S. Pat. Nos. 2,681,922, Balthis, June 22, 1954; 2,528,025, Whyte, Oct. 31, 1950; Chemical Abstracts 38 6180; 84 80436u; 48 6698; 57 13224; 47 3660; 60 2330; 49 15266; 54 5126; 50 14322; and 46 6468.

The use of propionitrile in various liquid phase extraction processes involving glycerides, fatty acids, and the like, is disclosed in U.S. Pat. Nos. 2,316,512, Freeman, Apr. 13, 1943; 2,200,391, Freeman, May 14, 1940; 2,313,636, Freeman, Mar. 9, 1943; 2,390,528, Freeman, Dec. 11, 1945; and Canadian Pat. No. 488,250, Freeman, Nov. 18, 1952.

Various miscellaneous references relating to the use of cyano compounds or amines of various types in the preparation of carboxylic acids and general references to the use of acetonitrile as a solvent are as follows: U.S. Pat. Nos. 2,042,729, Ralston and Poole, June 2, 1936; 3,828,086, Kenney and Donahue, Aug. 6, 1974; 3,519,657, Olah, July 7, 1970; 2,211,941, Sullivan, Aug. 20, 1940; 1,833,900, Hoyt, Dec. 1, 1931; 2,402,566, Milas, June 25, 1946; 2,640,823, Gloyer and Vogel, June 2, 1953; 2,895,974, Case, July 21, 1959; and Chemical Abstracts 53 9642.

Processes for manufacturing modified oil products from fatty oils, for manufacturing soap compositions, and for preparing metallic salts of higher fatty acids, which are carried out under anhydrous conditions or with the use of organic solvents of various types are disclosed in the following references: U.S. Pat. Nos. 1,957,437, Auer, May 8, 1934; 3,376,327, Freeland, Apr. 2, 1968; 2,271,406, Thurman, Jan. 27, 1942; 2,383,630, Trent, Aug. 28, 1945; 3,476,786, Lally and Cunder, Nov. 4, 1969; Chemical Abstracts 53 20838; 26 5875; 52 7743; and 53 20850.

German Patentschrift 1,254,139, May 30, 1968, discloses a process for preparing saturated fatty acids by reacting an α-olefin with a stoichiometric excess of acetonitrile, or acetate reagent, in the presence of an organic peroxide.

Reactions involving alkyl nitrile solvents are disclosed in U.S. Pat. No. 3,133,942, Hahl, May 19, 1964; and U.S. Pat. No. 2,753,364, Boner and Breed, July 3, 1956. The U.S. Pat. No. 3,133,942 relates to the production of metal salts of organic acids and, as disclosed therein, is carried out by using an organic acid and certain metals in the form of metal powders. Inert organic solvents, including acetonitrile, propionitrile and benzonitrile, are disclosed for use in the process. The process differs from that of the present invention in that it involves the use of metal powders, not alkali metal hydroxides, and thus does not appear to encompass the formation of super bases in the manner of this invention. Moreover, many of the solvents disclosed as being useful in the U.S. Pat. No. 3,133,942 are not contemplated for use herein.

The Boner, et al., patent, above, relates to a method for manufacturing lithium soaps (lubricating greases) using lithium carbonate and free fatty acids as the starting materials. Acetonitrile, benzonitrile and "benzyl cyanide" are taught to be useful solvents in the process, along with many other organic solvents. It will be appreciated that this reference does not disclose super bases comprising combinations of alkali metal hydroxides and alkyl nitriles in the manner of this invention, and is almost unlimited as to the type of organic nitrogen-containing materials suggested for use as the solvent medium.

The review article *Khim. Prom.* (Moscow) 1968 44 (10) 722-6 (Russ.), in abstract form (C.A. 70 28299y), is said to relate to the use of MeCN as a solvent, its reactions with aldehydes, ketones, alcohols, dienes and organic acids, substitution reactions and with inorganic compounds, and cites 90 references.

Attention is also directed to the review article by E. J. Fischer, *Allgem. Oel-u. Fett-Ztg.* 33, 78-81 (1936) which, in abstract form (C.A. 30 3539), is said to relate to methods for preparing acetonitrile and its use, principally as a solvent.

SUMMARY OF THE INVENTION

The present invention encompasses super base compositions of matter which comprise mixtures of alkali metal hydroxides and alkyl nitriles. The super base compositions herein provide an excellent reactant or catalyst for use in many commercially important chemical reactions which involve the use of strong bases.

The super bases of this invention provide a means for preparing carbanion or carbene reaction intermediates which comprises contacting an organic compound having at least one reactive (usually non-aromatic) C—H group with a super base of the present type. Thus, the present compositions are useful in a great variety of organic reactions which involve such intermediates.

As disclosed in the concurrently-filed applications of Peterson, cited hereinabove, compositions comprising alkyl nitriles and alkali metal hydroxides are also exceptionally useful for saponifying acid esters, as in soap making processes.

The super bases herein are also useful in reactions involving carbonyl compounds, e.g., Aldol Condensations (catalytic amount of super base) and in the Cannizzaro Reaction (aldehyde disproportionation involving stoichiometric amounts of super base).

As can be seen from the foregoing, the super bases of this invention find use in all manner of chemical reactions which proceed under strongly basic conditions or with a strong base as the catalyst.

DETAILED DESCRIPTION OF THE INVENTION

The super base compositions herein comprise mixtures of alkali metal hydroxides and alkyl nitriles. These super bases are useful in a wide variety of organic syntheses, especially in processes for preparing soaps and greases from animal or vegetable fats and oils.

By "alkali metal hydroxide" herein is meant lithium hydroxide, sodium hydroxide, potassium hydroxide, rubidium hydroxide, and cesium hydroxide. Sodium hydroxide and potassium hydroxide are especially useful for preparing super bases for use in the Peterson soap-making process, and sodium hydroxide is preferred for this use. Lithium hydroxide/alkyl nitrile super bases are especially useful for preparing lubricating greases from fatty esters or, preferably, hydroxyl-substituted fatty esters.

By "alkyl nitrile" herein is meant a compound of the formula RCN, wherein R is a linear, branched chain or cyclic aliphatic substituent. Typical examples of such materials are acetonitrile and propionitrile, which are preferred for use herein. Aromatic nitriles, e.g., benzonitrile, have been found not to be useful for preparing super bases in the present manner and are not encompassed by the present invention. Acetonitrile is the most highly preferred alkyl nitrile for use herein.

By "substantially water-free" herein is meant the circumstance wherein water is not intentionally added to the alkyl nitrile/alkali hydroxide mixture. Some water may be present, inadvertently, but this usually only constitutes a small percentage in the system. For example, the alkali metal hydroxides, especially LiOH, which is commercially available as the monohydrate, are somewhat hygroscopic and carry some moisture into the super base system.

By "carbanion" herein is meant a (generally transitory) species of the type:

wherein M+ is a counterion, e.g., Na+, Li+, etc.

By "carbene" herein is meant a (generally transitory) species of the type:

By "non-aromatic C—H group" is meant a covalently bonded carbon-hydrogen moiety which is not part of an aromatic bond system or extended conjugated bond system having substantial aromatic bond qualities. Any compound having a C—H bond which exhibits some acidic character in the presence of the super bases can be used in the practice of this invention to prepare carbanions or carbenes, but non-aromatic compounds are preferred.

By "animal or vegetable fats and oils" herein is meant the organic acid glyceride materials which can be secured from a wide variety of sources, including lard, tallow, coconut oil, palm oil, oils from oleaginous seeds such as soybeans, sunflower seeds, etc.

By the term "comprising" herein is meant that various other, compatible ingredients can be present in the present super base compositions, as long as the critical alkali metal hydroxide and alkyl nitrile are present. The term "comprising" thus encompasses and includes the more restrictive terms "consisting of" and "consisting essentially of" which can be used to characterize the essential components (alkali metal hydroxide and alkyl nitrile) of the super bases.

All percentages herein are by weight, unless otherwise specified.

The super base compositions herein are prepared by simply admixing the alkyl nitrile and the alkali metal hydroxide in any suitable vessel. It is to be understood that the alkali metal hydroxides are not particularly soluble in the alkyl nitrile reaction medium. Apparently, some alkali metal hydroxide does dissolve in the alkyl nitrile to provide the super base material. During a reaction involving the super base, additional alkali metal hydroxide apparently continually dissolves in the alkyl nitrile as previously formed super base is exhausted. It is preferred to use alkali metal hydroxides which have been ground to an appropriate particle size to aid in dissolution in the alkyl nitrile. This is not critical to the practice of this invention, but only makes the formation of super base more convenient and efficient. In the practice of this invention, the alkali metal hydroxides can be used as particles which pass through a 50 mesh sieve.

In an alternate mode, the super base compositions of this invention can be prepared by using a concentrated solution of the alkali metal hydroxide, rather than the powdered form. For some purposes, the use of solutions of the hydroxides, especially aqueous solutions, is an economic advantage. For example, concentrated, aqueous solutions of sodium hydroxide are commercially available and are especially suitable for use with alkyl nitriles to provide super bases for preparing soaps from animal or vegetable fats and oils by the Peterson soap making process.

When employing solvents for the alkali metal hydroxides, liquids such as water, the lower alcohols, and the like, which dissolve greater than about 30% by weight of the alkali metal hydroxide are preferred. It will be appreciated that the use of excessive amounts of solvents, especially organic solvents, for the alkali metal hydroxides may cause an undesirable dilution of the alkyl nitrile, which is the primary medium in which the super bases are formed. Moreover, solvents which are miscible with the alkyl nitrile may solvate the OH$^-$ ion and reduce its activity as a super base. Thus, the use of excessive amounts of such solvents is preferably avoided to assure that super bases are secured in undiluted, active form.

For most purposes, concentrated, aqueous solutions comprising about 50%, or greater, of the alkali metal hydroxide can be used herein without suffering a deleterious effect. This is primarily because the aqueous hydroxide solution is substantially immiscible with the alkyl nitrile and a heterogeneous reaction mixture is secured. Under such conditions a finite quantity of the alkali metal hydroxide dissolves in the reaction medium to provide a base of slightly diminished reactivity relative to the base realized when powdered alkali metal hydroxides are employed to prepare super bases under substantially water-free conditions, as disclosed hereinabove.

The super base compositions herein are used in a manner similar to any organic base reactant. For example, in a soap making process the mixture of alkyl nitrile and alkali metal hydroxide (either powdered or in aqueous solution) is admixed with, for example, a fatty acid glyceride, using any standard apparatus. The super bases herein are so much more reactive than their aqueous base analogs that their reactions, e.g., saponification reactions, proceed spontaneously and rapidly. In some instances, gentle warming can be used to initiate the reaction, which then usually proceeds substantially to completion without additional external heat being applied. Intermittent heating can be applied to maintain refluxing and to increase yield.

While not intending to be limited by theory, it appears that alkali metal hydroxides and alkyl nitriles may interact to form super bases in either of two ways. The simplest mechanism that might be proposed is one wherein the alkyl nitrile simply dissolves a small portion of the alkali metal hydroxide to form a highly reactive, relatively unsolvated hydroxyl ion. As this relatively unsolvated species is exhausted during a reaction, additional metal hydroxide dissolves, etc., to provide a constant source of relatively unsolvated OH$^-$.

Another proposed mechanism involves the interaction of the alkali metal hydroxides and alkyl nitrile to form an ambient anionic species (I) which, in turn, acts as a super base intermediate. It will be appreciated that the existence of such an intermediate is transitory and, according to standard practice, is inferred from stable reaction products which are formed therefrom. As illustrated by the following proposed reaction sequence, a mixture of sodium hydroxide and acetonitrile reacts with chloroform to form, in turn, reactive carbanion (II) and carbene (III) intermediates which, in turn, are "trapped" by cyclohexane, with the formation of the stable, isolable 7,7-dichloro-bicycloheptane. It is particularly noteworthy that literature preparations of dichlorocarbenes indicate that, with aqueous sodium hydroxide, yields of only about 5% of the reaction product are secured even after a 24-hour period. Using the present super base composition, a 58% yield of 7,7-dichlorobicycloheptane was achieved after only 45 minutes. This demonstrates the exceptional utility of the present compositions in this type of reaction.

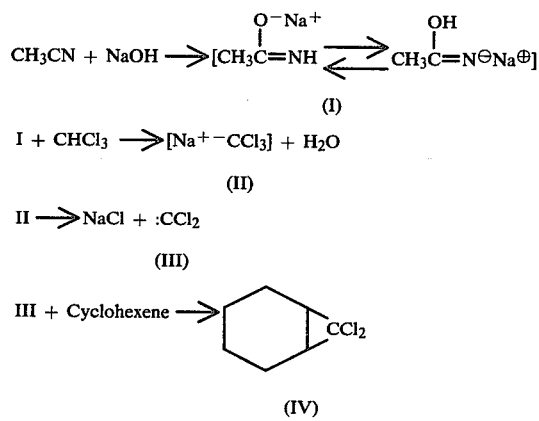

In the saponification of organic acid esters by the Peterson soap making process, the proposed mechanism is as follows, wherein R' and R" are all manner of alkyl, aryl and substituted alkyl and aryl groups:

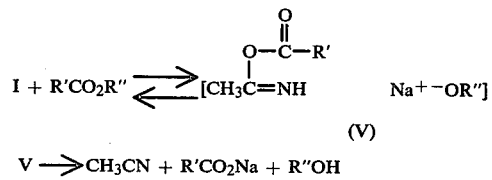

The super base compositions herein encompass all mixtures of alkyl nitriles and alkali metal hydroxides. Such mixtures having weight ratios of alkyl nitrile:alkali metal hydroxide in the range of from about 1000:1 to about 50:1 are useful in base-catalyzed reactions (e.g., aldol condensation) whereas such mixtures in the range of from about 50:1 to about 1:1 are conveniently used in reactions which involve a stoichiometric amount of base (e.g., saponification). Weight ratios of alkyl nitrile:alkali metal hydroxide are easily adjusted to meet the particular needs of any given reaction. In most instances, it is convenient to use the excess alkyl nitrile as the solvent medium for the primary reaction.

The following examples illustrate the practice of this invention but are not intended to be limiting thereof.

EXAMPLE I

Preparation of 7,7-dichloro-bicycloheptane

12 Grams (0.1 mole) of chloroform, 25 grams (0.3 mole) of cyclohexene and 200 mls. of acetonitrile were placed in a 500 ml. reaction flask and heated to 55° C. Sodium hydroxide (8.2 grams; 0.2 mole) was pulverized and passed through a 50 mesh screen and added to the reaction solution.

20 ml. samples of the reaction mixture were taken every 15 minutes to follow the progress of the reaction by means of gas/liquid chromatography. The reaction appeared to be complete after about 45 minutes at a temperature of 55° C.–60° C. The reaction was continued for a total of 1½ hours. The reaction mixture was thereafter poured into 500 mls. of water and extracted with diethyl ether. The diethyl ether was dried and evaporated. The distilled residue yielded 9.3 grams of the title compound, B.P. 79° C./13 mm Hg.

EXAMPLE II

Preparation of 2-propyl-2-hydroxymethyl-1,3-propanediol

To a heated (ca. 60° C.), rapidly stirred mixture of 9.9 grams (0.33 mole) of para-formaldehyde, 4.8 grams (0.12 mole) of finely pulverized, anhydrous sodium hydroxide, and 100 mls. of acetonitrile, was added, drop-wise, 8.4 grams of valeraldehyde. After drop-wise addition of the valeraldehyde had been completed, the reaction mixture was maintained at 80° C. for a period of ½ hour. At this time, 8.4 grams of insoluble solid (sodium formate and excess para-formaldehyde) was removed by filtration and discarded. Removal of the actonitrile solvent left 13.3 grams (88%) of a viscous oil which was identified as the title compound, B.P. ca. 140° C.–155° C./0.4 mm Hg.; recrystallized from a chloroform-acetonitrile mixed solvent, m.p. 100°–101° C.

EXAMPLE III

Preparation of Potassium Myristate

To a solution of 12.2 grams (0.05 mole) of methyl myristate in 120 mls. of acetonitrile was added 3.3 grams (0.05 mole) of finely pulverized 85% potassium hydroxide. The reaction mixture was stirred at substantially room temperature and monitored by following the rate of disappearance of methyl myristate by gas phase chromatographic analysis. After six hours, methyl myristate was no longer detectable. The precipitated sodium myristate was isolated by vacuum filtration and air dried overnight. A yield of 12.8 grams (96%) of solid potassium myristate product was secured.

In the process of Example III, the KOH is replaced by an equivalent amount of LiOH, NaOH, RbOH and CsOH, respectively, and the respective alkali metal soaps are secured.

The process of Example III is carried out with the acetonitrile being replaced by an equivalent amount of propionitrile, butyronitrile, n-pentylnitrile and cyclohexylnitrile, respectively, and equivalent results are secured. Super base reactions carried out in the higher alkyl nitriles (greater than about $C_6$ alkyl) are much slower than with the preferred lower alkyl nitriles.

EXAMPLE IV

Reaction of Triglycerides With Anhydrous Sodium Hydroxide

To a mixture of 50 grams (0.067 mole) of a 50:50 mixture of tallow and coconut fats in 250 mls. of acetonitrile at a temperature of 75° C., was added 8.15 grams (0.20 mole) of finely powdered 98% sodium hydroxide. The reaction was exothermic and refluxed vigorously, without extraneous heating, about two minutes after the addition of the sodium hydroxide. The reaction mixture was stirred at reflux temperature for a total of five minutes. During this time, a layer of fine, white, solid powdered material formed in the reaction vessel.

The solid material was collected by filtration and air dried overnight to give a yield of 46 grams (88%) of the sodium carboxylates (soaps) corresponding to the fatty acids in the starting material triglycerides.

In the process of Example IV the acetonitrile is replaced by an equivalent amount of benzonitrile ($C_6H_5CN$) and no apparent reaction occurs.

EXAMPLE V

Preparation of Lithium Carboxylate

To a suspension of 50 grams (0.054 mole) of hydrogenated castor oil in 250 mls. of acetonitrile at 70° C. was added 6.8 grams (0.162 mole) of lithium hydroxide monohydrate. The reaction mixture was stirred for 21 hours at reflux (81° C.). The product which precipitated from solution was isolated by vacuum filtration of the hot reaction mixture and was dried in a vacuum desiccator. Product yield was 49 grams (98%) of the corresponding lithium carboxylate, predominately 12-hydroxystearate, lithium salt.

As can be seen from the foregoing examples, the present super base compositions are useful both as catalysts (in the usual sense of that term) and in reactions involving a stoichiometric amount of base. Highly preferred super bases comprise acetonitrile and an alkali metal hydroxide, especially sodium hydroxide, in either a catalytic or stoichiometric amount depending on the intended use of the super base.

Whereas preferred super bases herein are those which are substantially water-free, the following example illustrates the use of super bases comprising a concentrated solution of alkali metal hydroxide and an alkyl nitrile. Concentrated aqueous solutions of NaOH and LiOH are preferred in this type of super base system.

EXAMPLE VI

Reaction of Triglycerides With Concentrated Sodium Hydroxide

To a mixture of 50 grams (0.067 mole) of a 50:50 mixture of tallow and coconut fats in 250 mls. of acetonitrile at a temperature of 75° C. is added 8.15 grams (0.20 mole) of sodium hydroxide dissolved in 8.15 grams of water. The reaction is initiated by gentle warming. Once initiated, the reactive mixture is maintained at reflux temperature, with stirring, for a total of five minutes. During this time, a layer of fine, white, solid powdered material forms in the reaction vessel.

The solid material is collected by filtration and air dried overnight (to remove acetonitrile solvent) to give a yield of ca. 90% of the sodium carboxylates (soaps) corresponding to the fatty acids in the starting material triglycerides.

In the process of Example VI the acetonitrile is replaced by an equivalent amount of benzonitrile ($C_6H_5CN$) and no reaction occurs.

In the process of Example VI, the acetonitrile is replaced by an equivalent amount of propionitrile, butyronitrile, n-decylnitrile, and cyclohexylnitrile, respectively, and equivalent results are secured.

In the process of Example VI the concentrated (50%) aqueous solution of NaOH is replaced by an equivalent amount of a 50% aqueous solution of LiOH and a solid, filterable, free-flowing lithium soap is secured.

As can be seen from the foregoing, the super base compositions herein are useful in a wide variety of chemical reactions, both as reactants and as catalysts. The super bases can also be employed as metal degreasing compositions, as paint removers, especially for oilbased paints, as oven cleaners, and for other uses wherein strong bases are commonly employed.

What is claimed is:

1. A substantially water free-super base reaction medium consisting essentially of a mixture of an alkali metal hydroxide and an alkyl nitrile selected from the group consisting of acetonitrile and propionitrile wherein the ratio of alkyl nitrile to alkali metal hydroxide is from about 1:1 to about 1000:1.

2. A composition according to claim 1 wherein the alkali metal hydroxide is a member selected from the group consisting of lithium hydroxide, sodium hydroxide and potassium hydroxide.

3. A composition according to claim 1 wherein the ratio of alkyl nitrile to alkali metal hydroxide is from about 1:1 to about 50:1.

4. A composition according to claim 1 which consists essentially of acetonitrile and powdered sodium hydroxide.

5. A composition according to claim 4 wherein the ratio of acetonitrile to sodium hydroxide is from about 1:1 to about 50:1.

* * * * *